US008198599B2

(12) United States Patent
Bouton et al.

(10) Patent No.: US 8,198,599 B2
(45) Date of Patent: Jun. 12, 2012

(54) DEVICE AND METHOD FOR DETERMINING ACTIVITY OF RADIOPHARMACEUTICAL MATERIAL

(75) Inventors: Chad E. Bouton, Delaware, OH (US); Arthur E. Uber, III, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 337 days.

(21) Appl. No.: 12/664,653

(22) Filed: Dec. 14, 2009

(65) Prior Publication Data
US 2012/0074330 A1 Mar. 29, 2012

Related U.S. Application Data

(63) Continuation-in-part of application No. PCT/US2009/046437, filed on Jun. 5, 2009.

(51) Int. Cl.
*G01J 1/42* (2006.01)
(52) U.S. Cl. ........................................................ 250/393
(58) Field of Classification Search .................. 250/393, 250/364
See application file for complete search history.

(56) References Cited

U.S. PATENT DOCUMENTS

| 3,790,804 | A * | 2/1974 | Hunt ........................... 250/506.1 |
| 4,968,305 | A | 11/1990 | Takahashi et al. |
| 4,994,012 | A | 2/1991 | Nakayama et al. |
| 5,472,403 | A | 12/1995 | Cornacchhia et al. |
| 6,767,319 | B2 | 7/2004 | Reilly et al. |
| 2004/0254525 | A1 | 12/2004 | Uber et al. |
| 2004/0260143 | A1 | 12/2004 | Reilly et al. |
| 2008/0038839 | A1 | 2/2008 | Linder et al. |
| 2008/0131362 | A1 | 6/2008 | Rousso et al. |
| 2008/0177126 | A1 | 7/2008 | Tate et al. |

FOREIGN PATENT DOCUMENTS

| DE | 4438361 | 2/1996 |
| EP | 0333276 | 9/1989 |
| EP | 1616587 | 1/2006 |
| GB | 2299162 | 9/1996 |
| JP | 2000 350783 | 12/2000 |
| JP | 2005 024291 | 1/2005 |

(Continued)

OTHER PUBLICATIONS

Automatic and Remote Controlled Ictal SPECT Injection for Seizure Focus Localization by Use of a Commercial Contrast Agent Application Pump, Feichtinger, et al., Blackwell Publishing Inc., pp. 1409-1413, 2007.

(Continued)

*Primary Examiner* — Kiho Kim
(74) *Attorney, Agent, or Firm* — Jill Denesvich

(57) ABSTRACT

A detector system measures radioactive material. A fluid path receives at least one aliquot of radiopharmaceutical. The fluid path locates the aliquot within a positioner formed with a concave configuration. A detector is located at an axial distance from the concave surface and determines the level of radioactivity of the aliquot. Alternatively, the fluid path may be less concave and a variable attenuator may be placed between the fluid path and detector. The variable attenuator may have a concavity that is based on the concavity of the fluid path so that the detector's ability to read the radioactivity is optimized. A method for forming an aliquot of radiopharmaceutical in a concave fluid passage. Positioning a detector located a distance from the concave surface to optimize reading spectral energy of the aliquot and activity is determining activity regardless of the position of the aliquot in the passage.

19 Claims, 13 Drawing Sheets

FOREIGN PATENT DOCUMENTS

WO 2004/004787 1/2004

OTHER PUBLICATIONS

Ictal SPECT Using an Attachable Automated Injector: Clinical Usefulness in the Prediction of Ictal Onset Zone, Lee et al., Informa Healthcare, Acta Radiologica, pp. 1160-1168, 2009.

International Search Report from counterpart PCT Application No. PCT/US09/46437 dated Aug. 11, 2009.
Counterpart European Search Report EP 10015627, Jun. 16, 2011.
Counterpart Partial European Search Report EP 10015627, Mar. 23, 2011.

* cited by examiner

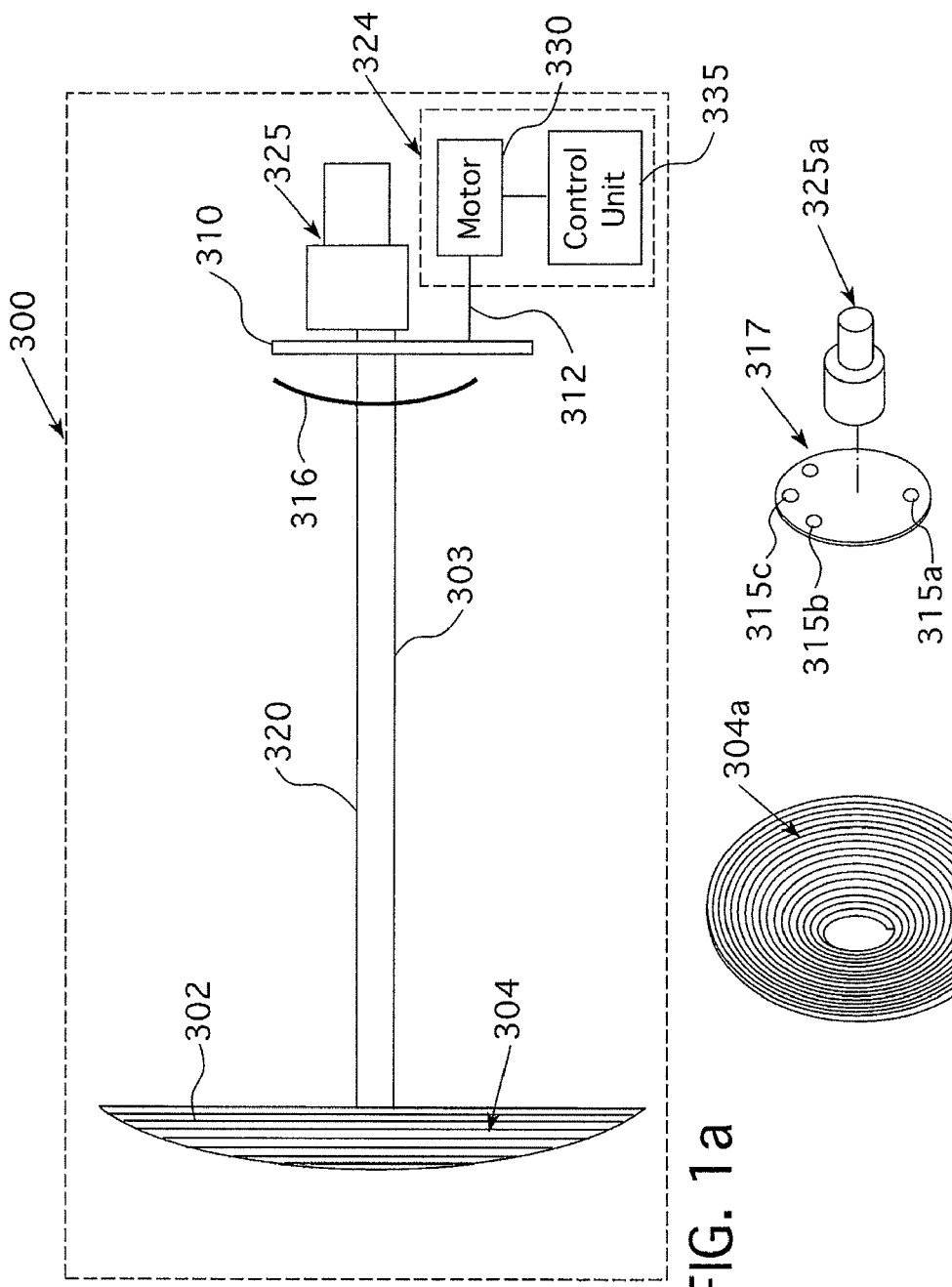

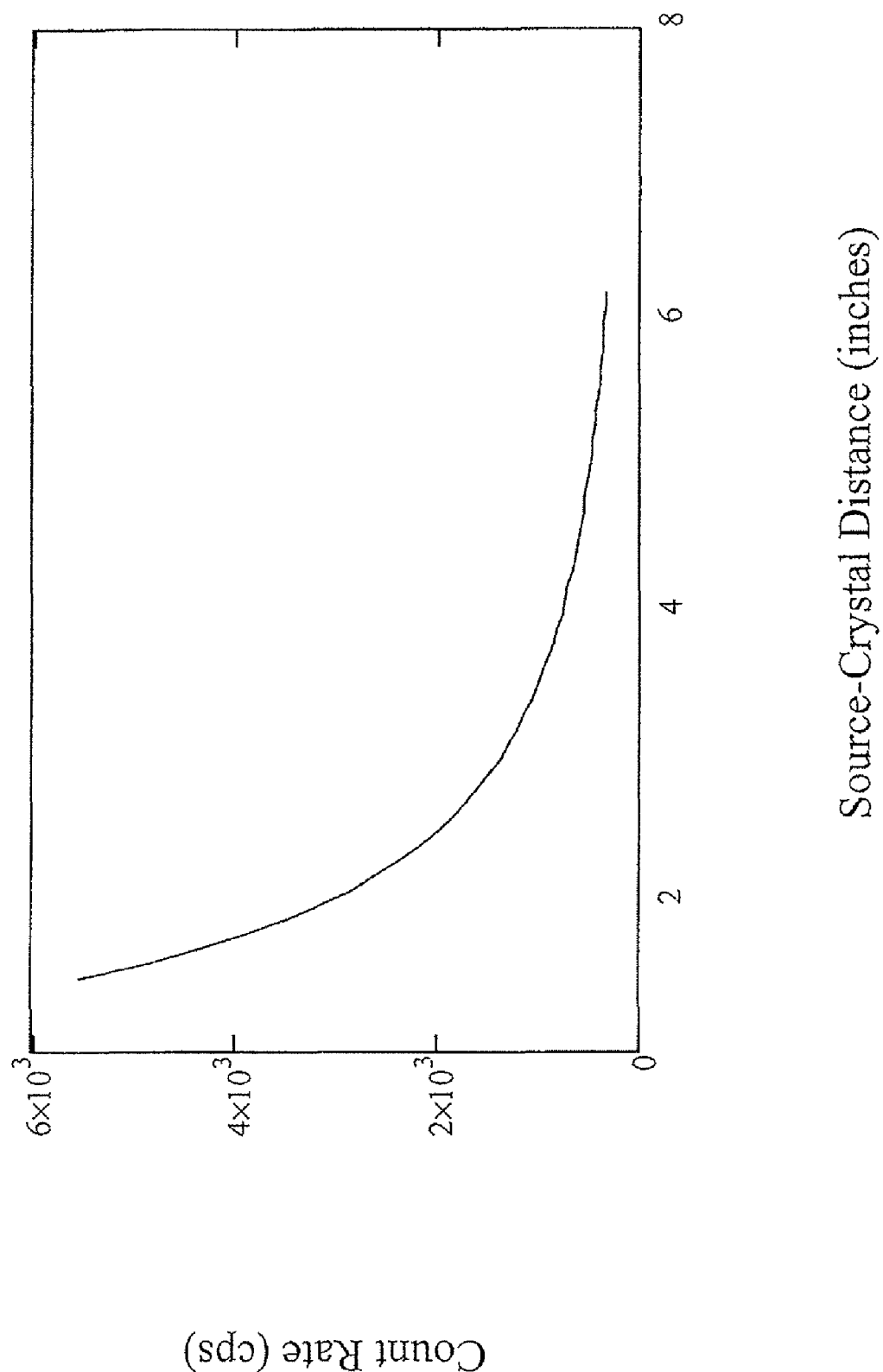

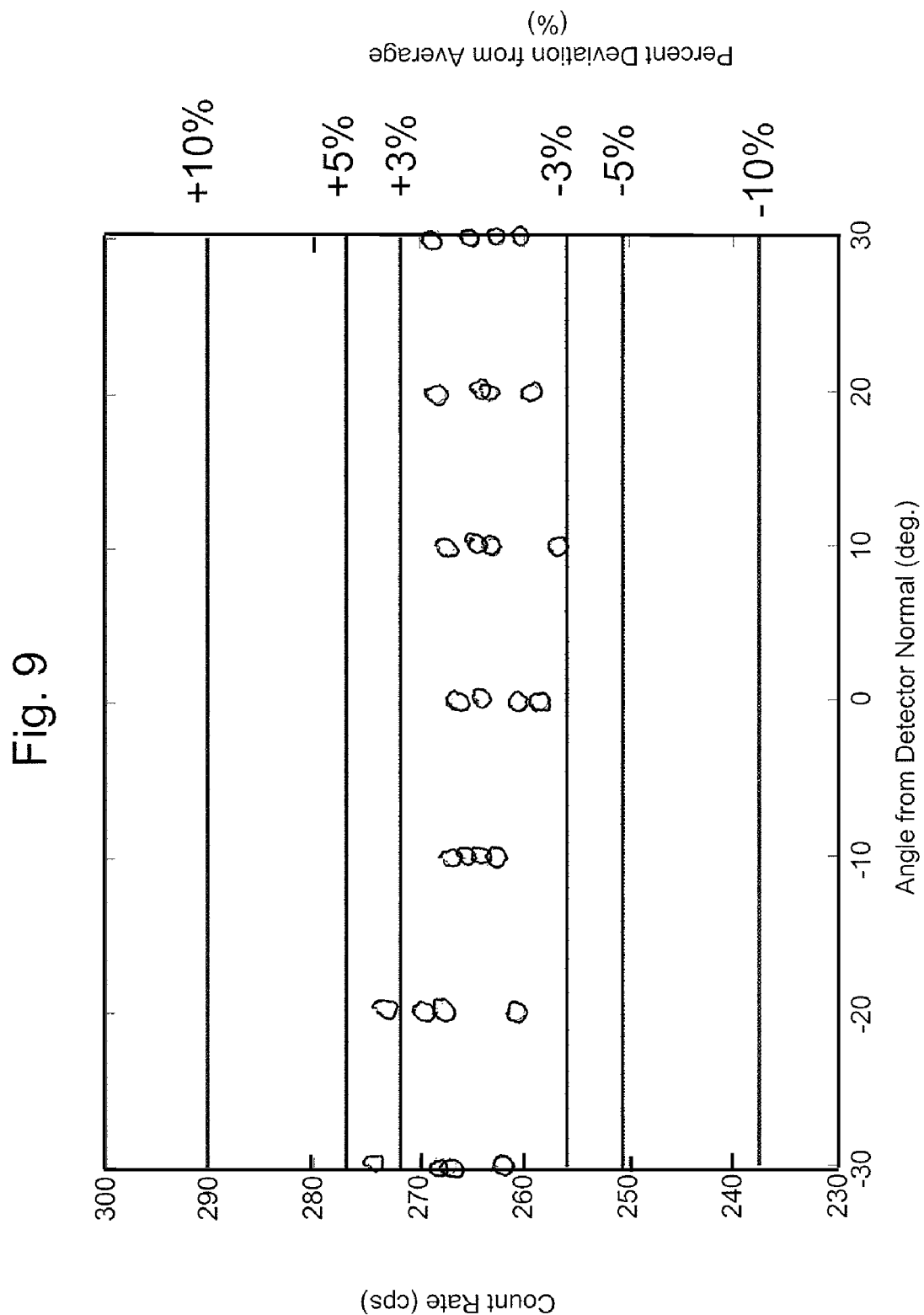

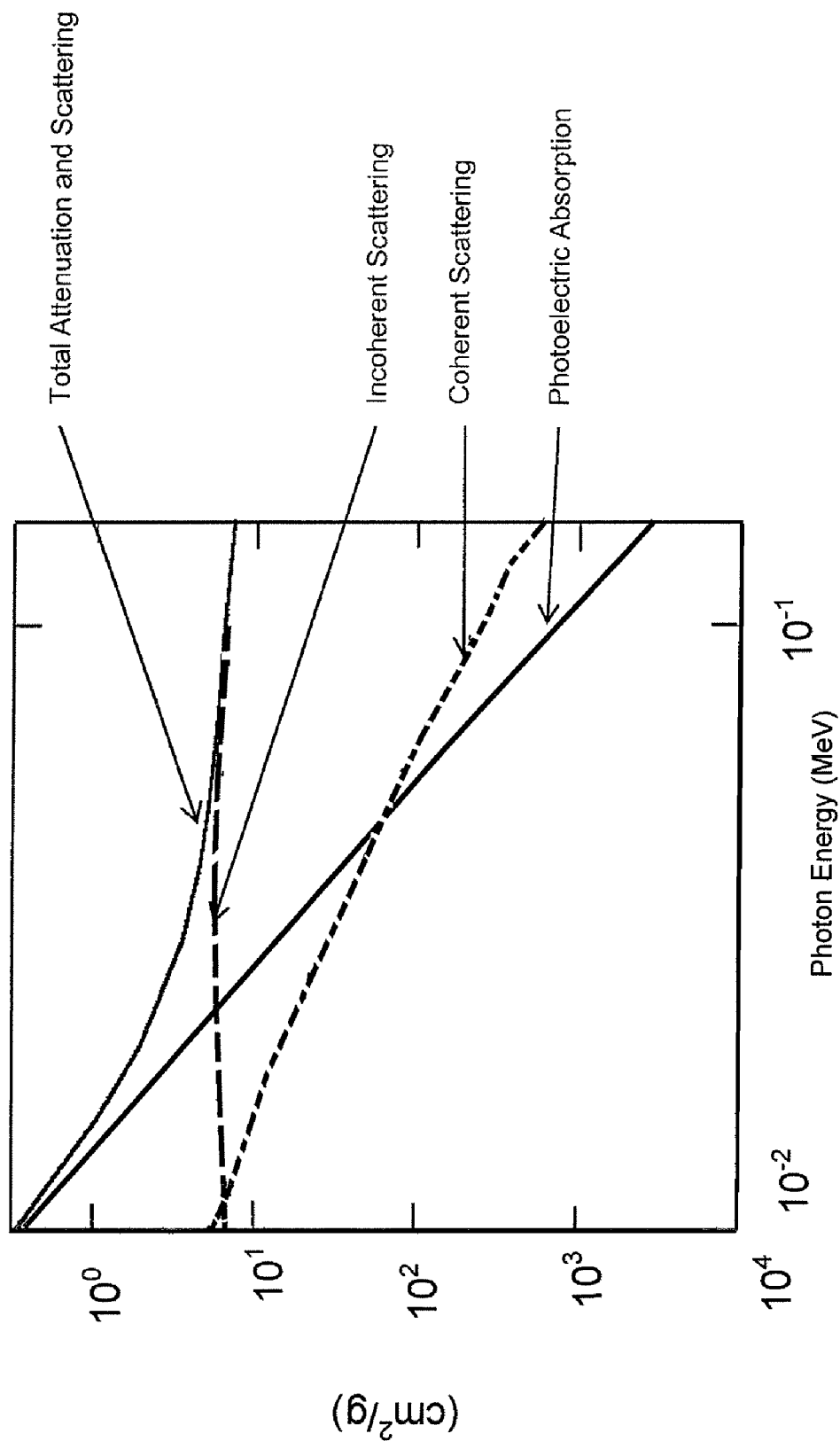

DEVICE AND METHOD FOR DETERMINING ACTIVITY OF RADIOPHARMACEUTICAL MATERIAL

This application is a Continuation-in-Part of PCT Application Ser. No. PCT/US2009/46437, filed on Jun. 5, 2009, the contents of which are incorporated herein by reference.

BACKGROUND OF THE INVENTION

The present invention relates to delivery methods, systems, and components thereof, for use with radiopharmaceutical materials, and especially with methods and components used for the determination of the radiation content of an aliquot of a radiopharmaceutical material for delivery.

Radiopharmaceutical materials are well known in the medical field for both therapeutic as well as diagnostic purposes. Encapsulated radiopharmaceutical materials (as "seeds") have been inserted into solid tumors such as prostate tumors to irradiate and thereby kill the tumor cells. Brief exposure of luminal cells in blood vessels to radioactive materials (held in place with a balloon catheter) after angioplasty has been used to reduce the incidence of restenosis in the blood vessel.

In addition to these therapeutic uses, radiopharmaceuticals can act as tracers in specific imaging techniques to help diagnose tissues requiring medical intervention. Two such imaging techniques are positron emission tomography (PET) and single photon emission computed tomography (SPECT). In PET imaging, a radiopharmaceutical that carries a positron emitting nuclide (such as $^{18}$F) is injected into a patient's vasculature. The positron emitted by the radionuclide collides with electrons in its vicinity, releasing a pair of gamma rays with opposing trajectories. The paired gamma rays are detected by sensors disposed on opposite sides of the patient, and the location of the radiopharmaceutical is thus determined. As an example, $^{18}$F-flourodeoxyglucose (FDG) is routinely used to detect tumor cells which preferentially take up the FDG. In SPECT imaging, the radiopharmaceutical carries a radionuclide that emits a single gamma ray photon during its disintegration. As with PET, the gamma ray is detected by sensors disposed about a patient and the location of the radiopharmaceutical is determined. As an example, $^{99m}$Tc sestamibi is administered into a patient's vasculature and monitored as the nuclide passes through the heart. This method provides a cardiologist with information regarding how well the heart is able to eject blood from the ventricles.

While the radiation dose from a diagnostic radiopharmaceutical is minimal for a single patient undergoing a single imaging procedure, the cumulative dose for either a medical technologist or physician who injects the tracer may be substantial. This is due to the number of patients the technologist or physician is required to inject on a daily basis. Consequently, a number of devices have been developed in order to help shield the physician or technologist from excess exposure to the radiopharmaceuticals. For manual injection of a radiopharmaceutical, syringes have been developed that incorporate shielding material in the body of the syringe (U.S. Pat. No. 4,968,305 to Takahashi et al.), and hand held shielded syringe holders have also been developed (U.S. Pat. No. 4,994,012 to Nakayama et al.). In addition to such manual devices, automated devices have also been described. Examples of such devices are found in U.S. Pat. No. 6,767,319 to Reilly et al. (herein incorporated by reference), PCT patent application publication WO 2004/004787 (Van Naemen et al., herein incorporated by reference), EPO patent application publication EP 1,616,587 (Buck, herein incorporated by reference), and U.S. patent application publication 2008/0177126 (Tate et al., herein incorporated by reference). While the application for these devices is primarily directed to PET imaging (and more specifically the use of FDG), similar style devices may be used for injecting SPECT radiopharmaceuticals for SPECT imaging procedures.

Referring to Buck and Tate et al. specifically, the automated injectors comprise in general the following components. A source of a radiopharmaceutical such as a vial or other container is disposed within a shielded environment within the injector. A needle, cannula, or other access device is inserted into the container to allow access to the radiopharmaceutical material. A fluid pathway is further provided from the access device to a first pumping device which may include a syringe and activator, or peristaltic pump. A source of a nonradioactive flushing material such as saline is also provided with a second fluid path, which may be connected to a second pumping device, or may be in fluid communication with the first pumping device through a valve mechanism. In the example using a second pumping device, the output thereof may be in fluid communication with the output of the first pumping device via an auxiliary valve mechanism. The output end of the first pumping device is in fluid communication with a third fluid pathway which is disposed to pass through a radiation detector device such as an ion chamber. The third fluid pathway is connected to a second valve mechanism that controls the direction of the fluid therein to either a waste container, or to a delivery device which may deliver the radiopharmaceutical material to a receptacle or to a patient for medical purposes. A computer running appropriate software is able to control the actions of the first and second pumping devices via motor control devices, and in addition control the valve mechanisms. The injection device may also comprise a monitor to display information to a user (such as the amount of radiation detected by the radiation detector), as well as an input device to the computer (such as a keyboard) that permits the user to enter information regarding the operation of the injector.

From a functional perspective, such an automated device may be used in the following manner. A technologist or physician may load a container or vial prefilled with a solution containing a radioactive material into a shielded receptacle in the injector. The amount of radioactive material such as specific activity (reported for example as Bq or Ci per unit volume) may be imprinted on a label of the prefilled vial. Alternatively, the total activity of the vial (as Bq or Ci) may be presented on a vial with a known or presumed volume of fluid. Once the prefilled vial or container is loaded into the shielded receptacle, an access device is inserted into the container either manually by the physician or technologist, or automatically by the injector. Similarly, a source of the non-radioactive flushing material, for example from a container or a hanging bag, is provided as well. The physician or technologist may then connect the flushing material to a second fluid pathway provided in the injector. The various fluid paths within the injector may be purged of air using the non-radioactive flushing material by means of a pumping process. The air purging process results in the fluid paths being filled with the flushing material, so no air is present for use. Thereafter, the physician or technologist activates the injector in a manner to provide a dose of the radiopharmaceutical for delivery. A variety of methods may be chosen to program the injector to deliver the amount of radiation required for delivery. For example, the physician or technologist user may enter a total delivery volume of radiopharmaceutical via the interface device on the injector. Alternatively, the user may enter the total radiation activity for a final dose. In such an example, the software in the injector computer would have information regarding the specific activity of the liquid in the radiopharmaceutical source and perform such calculations so as to determine the final volume to deliver. If a human patient is the recipient of the dose, parameters related to the patient (such as height and weight) may be input into the injector. In such an example, the software in the injector computer may use such information to determine the proper amount of radiopharmaceutical to deliver as an activity, and thereafter compute the total volume from the radiopharmaceutical source to deliver. These examples are not taken as exhaustive, and other methods may be used to program the injector to deliver a particular volume of the radiopharmaceutical for delivery.

Once the volume of radiopharmaceutical has been determined, the injector energizes the appropriate pumping mechanisms to transfer the required volume from the container sourcing the radiopharmaceutical into the third fluid path from the first pumping mechanism. A pumping method is then activated to pump the flushing fluid from the flushing fluid source into the third fluid pathway such that the bolus of the flushing fluid acts to push the dose of radiopharmaceutical along the fluid path. By this means, the dose of radiopharmaceutical progresses along the third fluid pathway until it enters into proximity of the radiation detector. As described in Tate et al., such a radiation detector may comprise an ion detector. Such an ion detector is briefly described as an enclosed container with a central anode and a collecting cathode between which an electrical potential is applied. The detector container is filled with a detecting gas (such as argon). When the radiation emitted by the radiopharmaceutical enters the ion detector, it ionizes some of the gas which results in positive and negative charges. The negative charges are attracted to the collecting anode, and a current is thereby created from the charged particles. The current produced by the radiation detector is then further processed by electronics and software to provide a reading of the number of disintegrations per second (as Bq or Ci) measured. As a result, the injector is provided direct information regarding the amount of radiation provided by the dose of radiopharmaceutical being delivered by the injector. As described in Buck, if the measured activity of the dose does not constitute a sufficient quantity of radiopharmaceutical, the injector can be programmed to provide a second dose, which in conjunction with the first, will provide the correct amount of radioactive pharmaceutical to be dispensed.

Once the correct volume of radiopharmaceutical is present in the third fluid path, the complete radiopharmaceutical dose is pumped out of the injector through a delivery device to its final destination. In the event that a dose has a radiation activity in excess of that required, valve mechanisms can be activated in the injector to dump the dose into a waste repository for removal.

As described in the above example of an automated radiopharmaceutical injector, a gas ionization chamber is used to measure the amount of radiopharmaceutical delivered to an output container or patient. Typically, such ionization chambers are physically large and can add considerable expense to the cost of the injector. Element 160 in FIG. 1D of Tate et al. demonstrates the relative size of such an ionization chamber with respect to the rest of the components of the injector. The FIG. 1D further suggests there may be some difficulty in replacing the ionization chamber in the event it becomes faulty. For these reason, it is desirable to replace an ionization chamber with an alternative radiation detector which is both less expense and less physically bulky to provide the required radiation measurement for the injector.

SUMMARY OF THE INVENTION

The present invention broadly contemplates an improved system and method for measuring the activity of a radioactive pharmaceutical material within a fluid passage for use within an automated injection device. The system herein broadly contemplated comprises a fluid passage to contain an aliquot of the radiopharmaceutical disposed as a spatial surface, a radiation detector, and one or a plurality of optical elements placed along the photon path between the fluid passage and the sensor. Such a system may be disposed in the injector to receive an aliquot of a radiopharmaceutical pumped along a fluid path from a source in the injector. The system output may further be connected to an output assembly to provide the aliquot to a patient after its activity has been measured.

The fluid passage containing the radiopharmaceutical aliquot must be positioned in a geometry that optimizes the exposure of the radiation detector to the radiation emitted by the aliquot. It is therefore another aspect of this invention that an aliquot positioner proximal to the detector is formed having a geometry wherein the radiation emitted by an aliquot is detected with equal responsiveness regardless of the location of the aliquot within the aliquot positioner. The aliquot positioner may comprise, as non-limiting examples, a tubular conduit or a flexible bag, and the conduit or bag may be disposed to form a coiled, spiral, serpentine, linear or other passage between the positioner input and output. Considerations in the geometric optimization of the positioner may include, without limitation, the mean axial distance of the aliquot positioner from the center of the detector surface, as well as the overall disposition of the aliquot positioner in space, as either a planar or curved surface. Embodiments of such curved surfaces include, but are not limited to, parabolic, spheroidal, dual cubic, or more complex geometric surfaces.

The present invention further contemplates the use of a number of different radionuclides in the radiopharmaceutical (including but not limited to $^{201}$Tl, $^{99m}$Tc, or $^{82}$Rb). Thallium (Tl), technetium (Tc), and rubidium (Rb) are useful for evaluating myocardial perfusion, and determining cardiac output function. Each nuclide possesses a unique emission spectrum and is prescribed in a wide range of activity levels (Bq or Ci). Thus, a measuring system incorporating a geometrically fixed aliquot positioner with respect to the detector could experience detector saturation when a high activity level is used, while the detector response may be within normal operating range at the low activity end of the range (across the various activities and nuclides prescribed). It is therefore another aspect of this invention to include optical elements to restrict the radiation activity level from the pharmaceutical aliquot located in the aliquot positioner from fully impinging on the sensor surface. Such optical elements may include, but not be restricted to, one or a plurality of collimators, slits, apertures, thin shielding materials such as tungsten foil or sheet of lead, or any combination thereof. These optical elements may be adjustable either manually or automatically to prevent or reverse sensor saturation for a particular activity level of an aliquot of a radionuclide. Adjustments may be accomplished through placing one of a series of attenuators which may include differently sized apertures (varying diameter), pinhole collimators disposed on a rotating wheel in the photon path between the radionuclide and the sensor, or placing one of a series of slits milled into a slideable metallic fixture into the photon path, or placing one of a series of different thicknesses of shielding sheets/foils, or other such embodiments.

More complex attenuators may also include an array of collimating pinholes disposed on a variable attenuator, the pinholes or channels extending radially through the attenuator body, and possessing equal or variable diameters.

Aliquot positioners having a variety of flat or curved geometries may similarly be combined with optical elements possessing a variety of attenuation or collimation properties to form selectable positioners. Such selectable positioners may optimize detector performance for specific radionuclides or radionuclide activity levels.

An additional aspect of this invention includes a method to use such a system to measure the activity of a radiopharmaceutical aliquot within a positioner One embodiment of a method includes: injecting via an automated injector an aliquot of known volume of a radiopharmaceutical liquid into a flat or curved aliquot positioner proximal to a radiation detector with various photon restrictive optical elements therebetween, the positioner disposed in a geometric concave surface facing the detector to optimize the response of the detector to the radiation emanated by the radiopharmaceutical, transmitting the response of the detector to a computer resident on the injector, and calculating the specific activity of the aliquot from the volume and the response from the detector.

BRIEF DESCRIPTION OF THE DRAWINGS

FIG. 1a illustrates a detector system for measuring the radioactivity from an aliquot within a selectable positioner including a concave aliquot positioner and/or variable attenuator of the present invention, and a solid state sensor.

FIG. 1b illustrates a side view of concave aliquot positioner of FIG. 1a with a selectable attenuator.

FIG. 2 illustrates a theoretical response curve of a detector count rate dependent on distance from a radiation source to sensor.

FIG. 9 illustrates count rate experimental data for various points on the concave surface derived from the dual-cubic model, as a function of angular displacement using a 0.1 inch thick polycarbonate disc over the radiation source.

FIG. 10 illustrates scattering and absorption coefficients as a function of photon energy.

DETAILED DESCRIPTION OF THE INVENTION

Figure 1C:
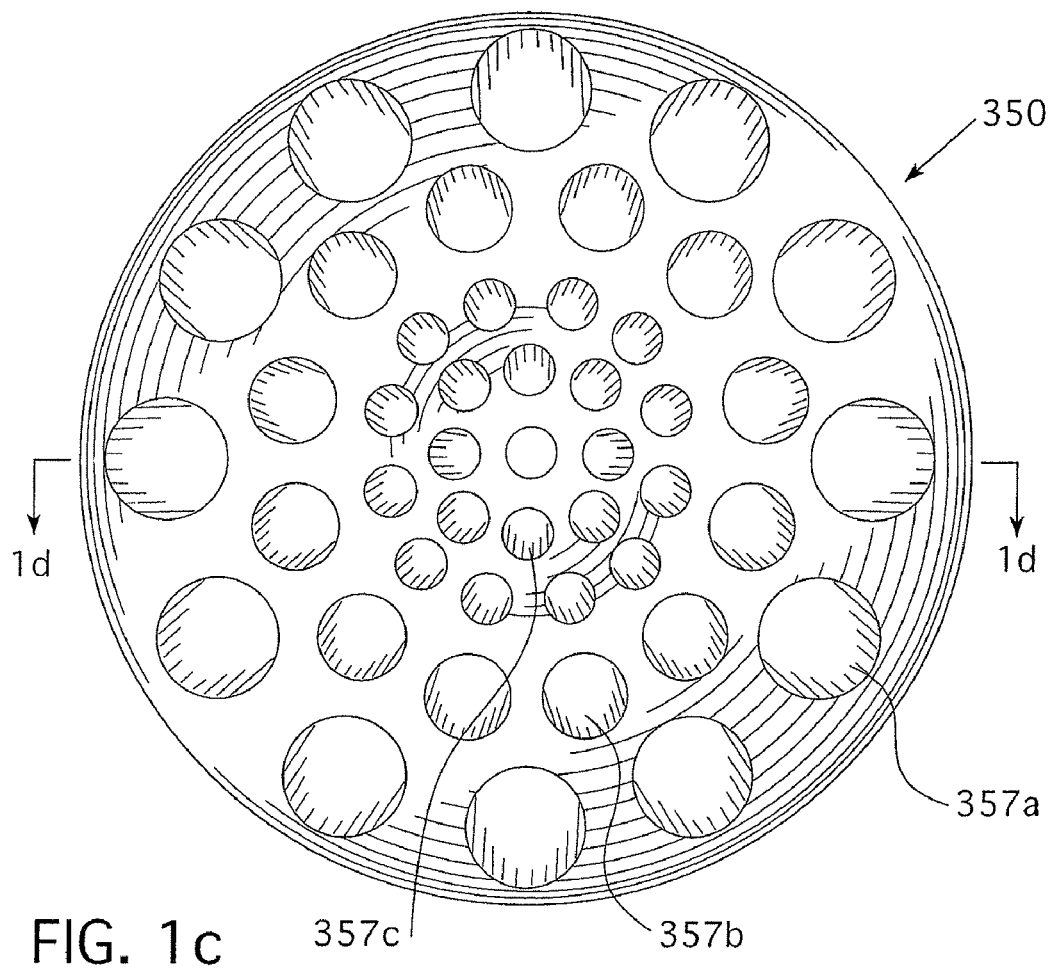
FIG. 1c illustrates a perspective view of an embodiment of a collimator array.

An embodiment of a detector system 300 for measuring the activity of an aliquot of a radiopharmaceutical is illustrated in FIG. 1a. As used in this disclosure, an aliquot refers to one or more volumes, boluses, slugs, or segments of fluid, either contiguous or separated by other materials that together form one or more than one doses for one or more than one patients. The detector system 300 includes a fluid pathway connected to a passage or aliquot positioner 302 formed with at least a concave surface 304. The aliquot positioner 302 is disposed a distance 320 from a radiation detector 325, comprising a sensor with a sensor surface along with electronics to condition the output from the sensor. A variable attenuator 316 can be disposed between aliquot positioner 302 and detector 325. The variable attenuator 316 along with the aliquot positioner 302 may each be shaped with a varied amount of concave curvature to form a selectable positioner. Accordingly, the aliquot positioner 302 positions the source emitting radioactive energy on a curved configuration and as the energy is emitted to the detector, the variable attenuator influences its path of travel to the detector. The variable amount of curvature in each optimizes energy that arrives at the detector. Additionally, selectable attenuator 310 can be disposed between aliquot positioner 302 and detector 325. An optional automated mechanism 324 can be connected to the attenuator 310.

The aliquot positioner 302 is formed in a unique concave surface 304 to permit a uniform radiation detection response. The distance from any point on the concave surface 304 to the detector 325, defined as the optical path 303, is derived so that a detector count rate is proportional to the aliquot radiation activity level regardless of the position of the aliquot along the aliquot positioner 302. A side view of concave surface 304a is provided in FIG. 1b. The concave surface 304a can take any of a number of forms, including but not limited to a parabolic surface, a spherical or spherical-like surface or more complex geometry depending upon the detailed geometric response of the detector 325 as will be illustrated below. The concave geometry is selected to maintain consistent sensitivity of the detector to the emitted radiation at various locations and at various radionuclide energy levels, and overcome the limitations that can exist for the spherical surface geometry.

Although a spherical surface is one example of a concave surface, it may not be suitable at certain energy levels and can result in an inaccurate activity measurement because an aliquot in a position near the outer radius of a spherical surface can cause a lower count rate than an aliquot at an inner part of the spherical surface or at its center. This difference can occur because the radiation emitted from the aliquot at the periphery of a spherical surface will strike the detector sensor surface at a non-normal angle, and thus reduce its effective count rate due to reduced detection surface area and/or change in effective absorption constant of the sensor based on the incidence angle of the radiation and/or a change in detector window (or optical path) attenuation and/or scattering levels.

The concave surface 304 has a "radius" that facilitates higher accuracy in the measurement of radioactivity detection. For a concave surface, the term "radius" as used herein refers to the distance from any point on the positioner to the sensor. The "radius" of the concave surface will be large compared to the potential relative position variations that could occur between the radiation fluid being measured and the sensor. The causes of this relative position variation include, but are not limited to, fluid radiation moving closer or further away from the sensor within the positioner, the aliquot positioner moving closer and further away from the sensor due to mechanical position errors, manufacturing variations, and sensor movement. Since small mechanical variations such as these are common in physical systems, it is advantageous to maintain this high ratio between the concave surface 'radius' and the sensor to maintain high measurement accuracy in spite of these small variations.

Aliquot positioner 302 may be formed of a tubular conduit that has a width or diameter that is preferably selected to minimize errors in the reading, and therefore is relatively small as compared to the 'radius' 320 (as previously discussed). In this way, if the radioactive portion of the fluid adheres to a wall, and therefore, moves to a position that is closer to the sensor or further away, the amount of measurement error will be reduced. The tubular conduit can be, for example, solvent or heat bonded together into the concave shape and then placed into a similarly shaped receiving surface (not shown).

In addition to minimizing errors caused by the location of the aliquot within the positioner, measurement errors due to positional misalignment of the positioner with respect to the radiation detector 325 can also be minimized by employing a sufficiently large optical path 303 between the positioner and the detector. The 'radius' or distance 320 may vary slightly due to mechanical tolerances from the nominal distance profile (which is determined by the specific concave geometry selected). This distance variation or perturbation affects the magnitude of the detection errors. A sufficiently large optical path 303 between the aliquot positioner and the detector will minimize detector errors.

Since the positioning of the conduit in the shape of a concave surface is important, it is preferable that there is some alignment mechanism for the positioner 302, which may include pins, grooves, ledge, lips, or other mechanical means (not shown). Alternatively, the aliquot positioner 302 can be attached to a more rigid plastic piece (not shown), either by entrapment in a groove or clips, or by bonding. The aliquot positioner can also be secured between two rigid, multiuse surfaces (not shown), or be made from two relatively rigid injection molded pieces that are then bonded together (not shown). Further, the positioner may be fabricated as a channel or tubular conduit that is machined or molded into low density material. Besides the tubular conduit, the aliquot positioner 302 can be fashioned from a receptacle that is formable into an adequate concave fluid path, for example, but not limited to a bag or other flexible container with an inlet and an outlet (not shown). The bag can also be compressed between two reusable surfaces (not shown) that create a coiled, serpentine or otherwise convoluted concave shape through which the fluid will flow.

As the detector system is designed to measure the radiation emitted by the radionuclide aliquot, the material comprising and the thickness of the aliquot positioner 302 are preferably designed to minimize radiation absorption. Materials that have such characteristics may be low density plastics. Some non-limiting examples of such material include polymers and various manufacturing and injection molding materials. Polycarbonate, for example, is often used for optical applications due to strength and ability to be molded accurately and consistently. FIG. 10 illustrates the various scattering and absorption effects due to interactions of photons of various energies with polycarbonate plastic. The radionuclides used in PET or SPECT imaging, can include $^{201}$Tl, $^{99m}$Tc, $^{123}$I, and the positron emitters $^{18}$F and $^{11}$C. The range in gamma ray energy from these sources includes 140 keV (for $^{99m}$Tc) to 511 keV for the gamma radiation released by positron annihilation. As is illustrated in FIG. 10, for energies close to those relevant for PET or SPECT imaging, incoherent scattering mechanisms present the most likely effect of polycarbonate plastic on the photons.

Regardless of the low density plastic used, such scatter may cause, for example, the gamma photons, leaving the plastic to diverge from their normal paths from the radiopharmaceutical aliquot. For this reason, the aliquot positioner wall may be sufficiently thin to reduce these scattering effects which can impact sensor accuracy across the energy range of interest. Thick-walled tubing may lead to excessive absorption at some energy ranges, and provide multiple scattering pathways for the emitted photons. Such multiple scatter may results in the aliquot appearing physically larger to the detector than its actual size. A variety of tubing diameters and wall thicknesses may be used to form the aliquot positioner, each of which may be specifically optimized for the range of radionuclide energies and dosing to be dispensed. For materials which may include, but not limited to, polyvinyl chloride, polyurethane, silicone, or coextruded nylon, the wall thickness for tubing may vary between 0.020 inches and 0.125 inches, and the tubing diameter may vary between 0.030 inches and 0.3125 inches. The aliquot positioner 302 preferably comes sterilized and as a preassembled unit.

The radiation detector 325 may use a variety of modern radiation sensing technologies appropriate for the energy range of interest. Non-limiting exemplary radiation sensing technologies include, a Si PIN or avalanche photodiode array (silicon PMT) with a scintillating material or cadmium-/zinc-/telluride (CZT) or cadmium/telluride crystal-based detectors. The CZT crystals with a high-gain charge amplifier provide stable and high efficiency performance. Such a sensor has the benefit of high sensitivity as well as small profile and low cost. The shape of the crystal may be optimized to provide axial symmetry so that as an aliquot travels along the passage the sensor's effective surface area should remain the same, collecting uniform radiation flux per unit time. Non-limiting examples of crystal shapes include circular or square profiles. A CZT detector comprises a CZT crystal (the sensor) across which an electric potential is applied via an anode and cathode. Incident gamma or x-rays (ionizing photons or photons herein) create electron-hole pairs which migrate to the anode and cathode respectively. The electrons travel much more quickly due to higher mobility and are collected at the anode typically through a blocking capacitor (which protects the charge amplifier from the high voltage bias present at the anode). The number of electron-hole pairs created is proportional to the energy of the photons absorbed by the crystal. In a short time constant/high-bandwidth transimpedance amplifier configuration, commonly used in counting applications and when spectra are being collected, a brief (few microseconds) pulse is created for each photon that is absorbed in the crystal. The height of the voltage pulse is proportional to the amount of charge collected which is again, proportional to the energy of the incoming photon. By collecting a suitable number of pulses and recording the pulse heights of the events, a histogram (or spectrum) can be formed, allowing the system to discriminate between radiation from $^{99m}$Tc and other radiopharmaceutical nuclides.

The radiation detector 325 can be mounted on a small circuit board (not shown), which also includes suitable electronics for its operation. Such electronics may include, but are not limited to, a source of a high electrical potential to place across the body of the sensor, current amplifiers for the output of the sensor, noise reduction circuit elements such as filters, and a means to provide the final conditioned signal from the detector to a computer that is included with the injector system. Such a CZT detector can be housed in an assembly, which can be small such as a 20 mm cube, and may be attached to a an appropriately sized circuit-board containing conditioning electronics to provide the required data for a computer to acquire and use (see for example the eV Microelectronics iGEM Sensor Module [http://www.evmicroelectronics.com/igemsm.html viewed 13 Nov. 2009]).

Further included in the radiation detector system 300 may be a selectable attenuator 310 disposed in the optical path 303 between the aliquot positioner 302 and detector 325 or an active surface of the sensor crystal. Selectable attenuator 310 is used to accommodate a large radiation level dynamic range while operating the sensor in the desired, linear, or optimum response range. Such desired response range is that which prevents sensor saturation or pulse pile-up at the high end, and prevents the sensor from operating in the noise or requires too long a time for determination of a measurement at the low end. As the specific activity of an aliquot of radiopharmaceutical can vary from one preparation to another, and because the total spectral energy may differ between pharmaceuticals comprising different radionuclides, the selectable attenuator 310 minimizes or prevents saturation of the radiation detector. Selectable attenuator 310 may comprise a rotating disc assembly 317 or a linear positioning device (not shown). Selectable attenuator 310 may include, but not be limited to one or a plurality of apertures, attenuators, slits, or channels. FIG. 1b illustrates a series of channels 315 a-c that are disposed at various locations about the disc 317. The channels may have different sized diameters. Additionally, the selectable attenuator 310 can comprise a series of attenuators comprised of materials of varying thickness or material that may be selected so that the maximum amount of radiation directed from the positioner does not exceed, or falls outside the linear range of the detector 325 response. Such attenuator material is preferably a high density material that has a high attenuation-to-scatter ratio, some non-limiting examples including lead, tungsten and gold. In another embodiment, the selectable attenuator may include a continuous strip of attenuating material of varying thickness. The foil may be fabricated to possess a variety of cross sections or profiles, including a flat or domed profile. The selectable attenuator may be positioner so that the thickness of the foil in the optical path is sufficient to assure that the detector response is within its linear range.

The selectable attenuator may also include a small constant calibrating radiation source, (not shown) facing the sensor, to provide a means of calibrating the detector response. In one non-limiting example, a small calibrating source sample of $^{243}$AM (half-life 7400 years, gamma energy 74.7 keV) or $^{241}$Am (half-life 432 years, gamma energy 59.5 keV) can be used as a constant source of radiation with known spectral characteristics. As an occasional check on the proper functioning of the detector, this calibrating source may be placed in front of the detector so that its response may be measured. Deviations from previous calibrations of the detector can be noted and used to determine if the detector requires replacement or recalibration. Selectable attenuator 310 can be positioner in an optimal way in the optical path 303 between the positioner 302 and the detector 325. This may be accomplished manually, through a user's hand positioning the element into place, or via an automated device.

An automated mechanism 324 may be connected to selectable attenuator 310, as illustrated in FIG. 1a. Selectable attenuator 310 may comprise a disc 317 on which the optical elements are disposed. The center of the disc 317 is connected to an axle 312 which is driven by a motor 330, such as a small DC motor or stepper motor. This motor is controlled by a control unit 335. The control unit may receive information from the injector computer (not shown), to activate the motor so that the appropriate optical element of the selectable attenuator is properly aligned in the optical path 303. Various means are contemplated to assure the appropriate optical element is properly aligned in the optical pathway, which may include but are not limited to the use of limit switches, fiducial markings, or motor encoders associated the motor 330.

The control unit 335 is in communication with a computer to choose a specific optical element. In one embodiment, the user may enter via an input device the name of the radiopharmaceutical, radionuclide, and/or activity level into the computer. The computer may have a database that cross-references an appropriate optical element with a specific input radiopharmaceutical or radionuclide name or activity level to optimize the detector response. This information may be further indexed to a control sequence sent to the motor control unit to place the appropriately indexed optical element into position. Alternatively, a known optical element may be placed initially in position, and the radiation detector may transmit its output data to the injector computer when an aliquot is presented in the aliquot positioner, the sensor providing a preliminary gross estimate ("sneak peak") of countrate via a short integration time measurement, The computer then may compare the data from the detector to data representing the response curve of the detector. If the detector data are outside a range representing the linear response of the detector, the computer may send a control sequence to the motor controller thereby positioning a new optical element to either increase or decrease the incident radiation on the detector. Alternatively, the detector may transmit data related to the spectral properties of the incident radiation to the injector computer. A database may be included in the computer containing data representative of the spectral properties associated with a number of potential radiopharmaceuticals. The detector data may be compared with this database to identify the appropriate radionuclide. An output of the computer on a monitor may provide this information to the user. At the same time, the computer may send appropriate control data to the motor control unit to place the proper optical element into the optical path to optimize the response of the radiation detector to that radionuclide.

Not only can the curve of the positioner 302 be varied to optimize the reading of the detector, but also a concave optical element 316 can be varied in curvature to affect the reading by the detector. The variable attenuator 316 can be shaped in a variety of concave profiles which would be similar to the aliquot positioner concave surface profiles discussed above. This curved shape of the variable attenuator 316 can reduce non-normal radiation photon propagation effects which could reduce sensor accuracy as the aliquot moves to different positions along the aliquot positioner. In fact, varying the curvature of each of the aliquot positioner and the variable attenuator can optimize the ability of the detector to sense the radiation. Therefore, the concave aliquot positioner and the variable attenuator 316 provide selectable positioning and adjustable compensation, respectively, for the radioactivity (or radioactive fluid) so that the radiation is optimally read by the detector. The concave optical element can be made of a high density radiation material that has a high attenuation-to-scatter ratio, some non-limiting examples include lead, tungsten and gold provide appropriate attenuation while preventing scatter, which would otherwise decrease sensor accuracy.

FIG. 1c illustrates a perspective view of an exemplary variable attenuator formed into a collimator array 350. Collimator array 350 includes channels 352 which may have diameters that are uniform or varied in size to obtain a more accurate detection of activity. Collimator array 350 has a concave shape and channel size variation, which depending on the variation in each, can enhance the ability of the detector to read the activity associated with the aliquot at a position in concave portion of the positioner. This enhancement is accomplished by a compensation for positional differences of the aliquot in the concave positioner.

Figure 1D:
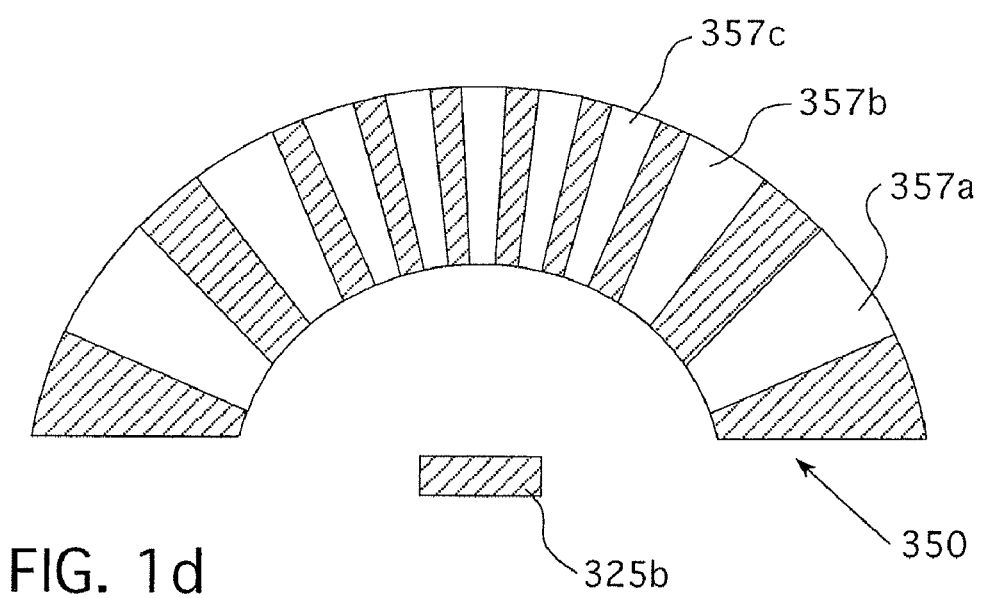
FIG. 1d illustrates a cross-sectional view of an embodiment of the collimator array of FIG. 1c.

FIG. 1*d* is a cross-sectional view taken along line 1*d*-1*d* of the collimator array 350 or "pin cushion" of FIG. 1*c*. In FIG. 1*d*, the collimator array 350 is placed an axial distance from detector 325*b* such that the inner concave surface faces the detector. For example, the channels at the periphery of the collimator array, such as channel 357*a*, have a larger diameter than the diameter of channels, such as channel 357*c*, found towards the center. Channels located between the center and the periphery of the collimator array, such as such as channel 357*b*, have a diameter size between those channels at the center and the periphery. The channels are drilled at an angle normal to both the outer and the inner surface of collimator array, thus having greater inclination angles for the channels at the periphery. This will create more uniform response for the detector, regardless of the position of an aliquot in the curved positioner, for a given activity. Collimator array 350 thus provides variable attenuation.

Figure 1E:
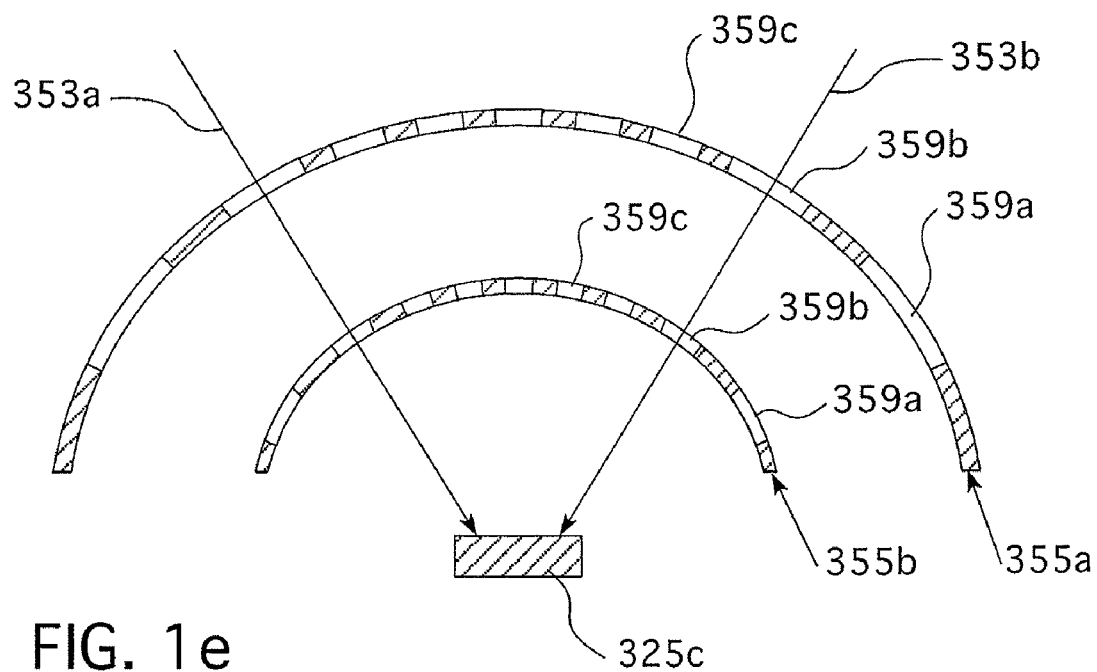
FIG. 1e illustrates a cross-sectional view of an embodiment of a dual collimator array.
Figure 1F:
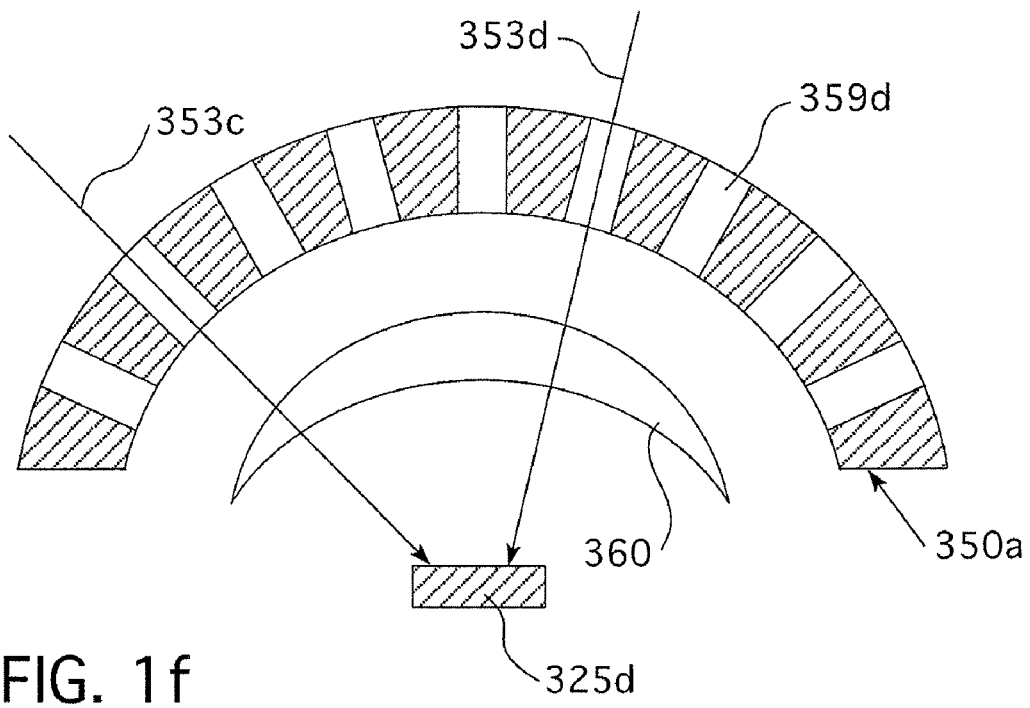
FIG. 1f illustrates a cross-sectional view of an embodiment of a collimator array with a domed attenuator.
Figure 1G:
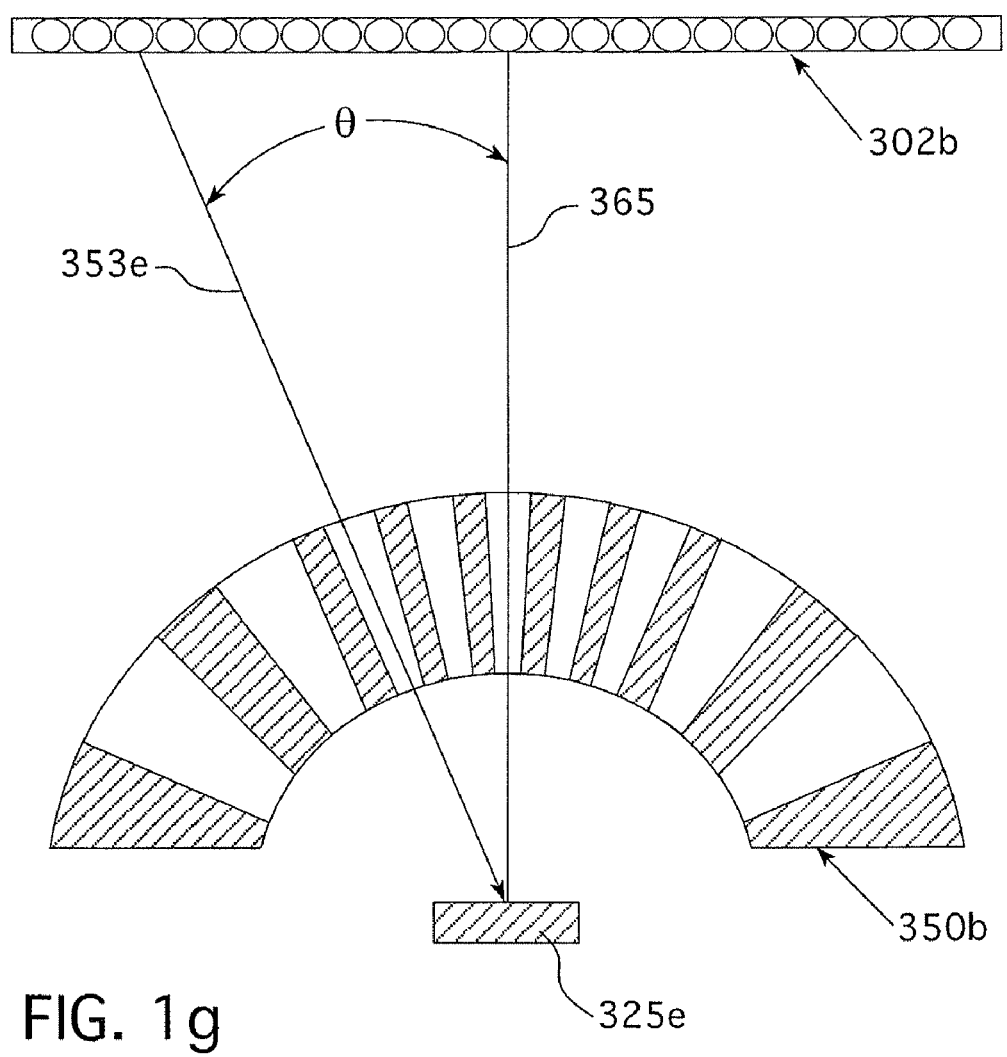
FIG. 1g illustrates a cross-sectional view of an embodiment of a collimator array with a flat aliquot positioner.

Further, with the curved collimator array the concavity of the aliquot positioner can be minimized or have no concavity and instead be a flat fluid path as shown in FIG. 1*g*. The detector system has an aliquot positioner 302*b* where the concavity is minimal or has no curvature and the collimator 350*b* is curved. The variation between the concavity or curvature of the positioner and the optical elements may be particularly advantageous for handling different nuclides or energy levels. If one concave positioner is not suitable across all energies/nuclides of interest (due to scatter variation), then a 'pin cushion' collimator array could be moved into place for a given nuclide (via rotational wheel or linear slides, as non-limiting embodiments). A variety of pincushions can be used, with a variety of patterns of collimating channels and channel diameters as well as cushion thickness, each of which may be optimized for a specific energy range of radionuclide.

As illustrated in FIG. 1*g*, collimator array 350*b* has channels which vary in size. Each of the channels can be located at positions measured at an inclination angles (shown as Θ). The greater the angle the channel is offset from the center line, 365, the larger the diameter of the channel. Collimator channels 357*c* centered at a midpoint of the curvature would have a smaller diameter as compared to channels 357*a* at the periphery. Channels, such as channel 357*b*, positioned between the center and the periphery of the array 350*b* similarly would have diameter sizes between those of the center and peripheral holes.

Collimator array 350 could be one continuous layer of shielding material, alternatively the collimator array could be two or more sufficiently thick shielding material pieces, such as 355*a* and 355*b*, as illustrated in FIG. 1*e*. Channels 359*a-c* may be punched or drilled of appropriate diameters to create equi-responsiveness of the detector for photons emitted by the aliquot in the positioner. A solid or single-piece collimator array could also be injection molded by from a moldable shielding material, such as those manufactured by Poly-One™, where lead powder is combined with a polymer.

A collimator array 350 may also be used with a curved attenuator 360 or other optical element, as illustrated in FIG. 1*f*. Such a collimator array 350 and curved attenuator could be utilized with an aliquot positioner not be disposed on a concave surface, but rather is disposed on a flat plane (as an example, 302*b* in FIG. 1*g*). A planar surface has the benefit of being easier to manufacture and mechanically control than a curved surface. The planar surface of the positioner may produce geometric distortions with respect to the surface of the detector 325*d*. In one distortion, the absolute distance of a radioactive aliquot from the detector increases as the aliquot is transferred to the periphery of the plane from the center. This decreases the cone of radiation incident on the detector. The second distortion is due to the midline of the cone of radiation not being normal to the surface of the detector. While the detector may respond to incident radiation not normal to its surface, such response will not be as efficient as that of radiation impinging at a normal angle. Since the surface of the detector is not normal to the midline of the incident radiation from an aliquot disposed on the periphery of the fluid element, the result is that the effective area of the detector surface will be reduced. A way to reduce these distortions is to deploy an attenuator 360 with non-uniform thickness in addition to a collimator array 350*a*, composed of channels, such as 359*d*, which all possess equal diameters. The thickness of attenuator 360 may vary in order to provide more attenuation in the middle (on axis) than at its periphery, thereby compensating for the differences in path length and solid angle of the photon flux impinging on the detector from the periphery of the plane compared to the center.

As illustrated in the FIG. 1*f*, photon trajectory 353*c*, originating from the periphery of an aliquot positioner, would pass through less attenuating material than trajectory 353*d*, originating closer to the center of the positioner. Attenuator 360 placed in proximity to the detector may enable the attenuator to be smaller in size than if it is placed closer to the aliquot positioner. This has the advantage of being easier to fabricate and mount. A second advantage to using the smaller attenuator nearer the detector is that it may be incorporated as a component of a selectable attenuator. In addition, different attenuators with different range of thickness can be used for different isotopes. Other combinations of attenuators, collimator arrays and other optical elements may be contemplated that may allow the sensor to operate in its linear response range over a wide range of aliquot activities and radionuclide spectra.

Figure 3:
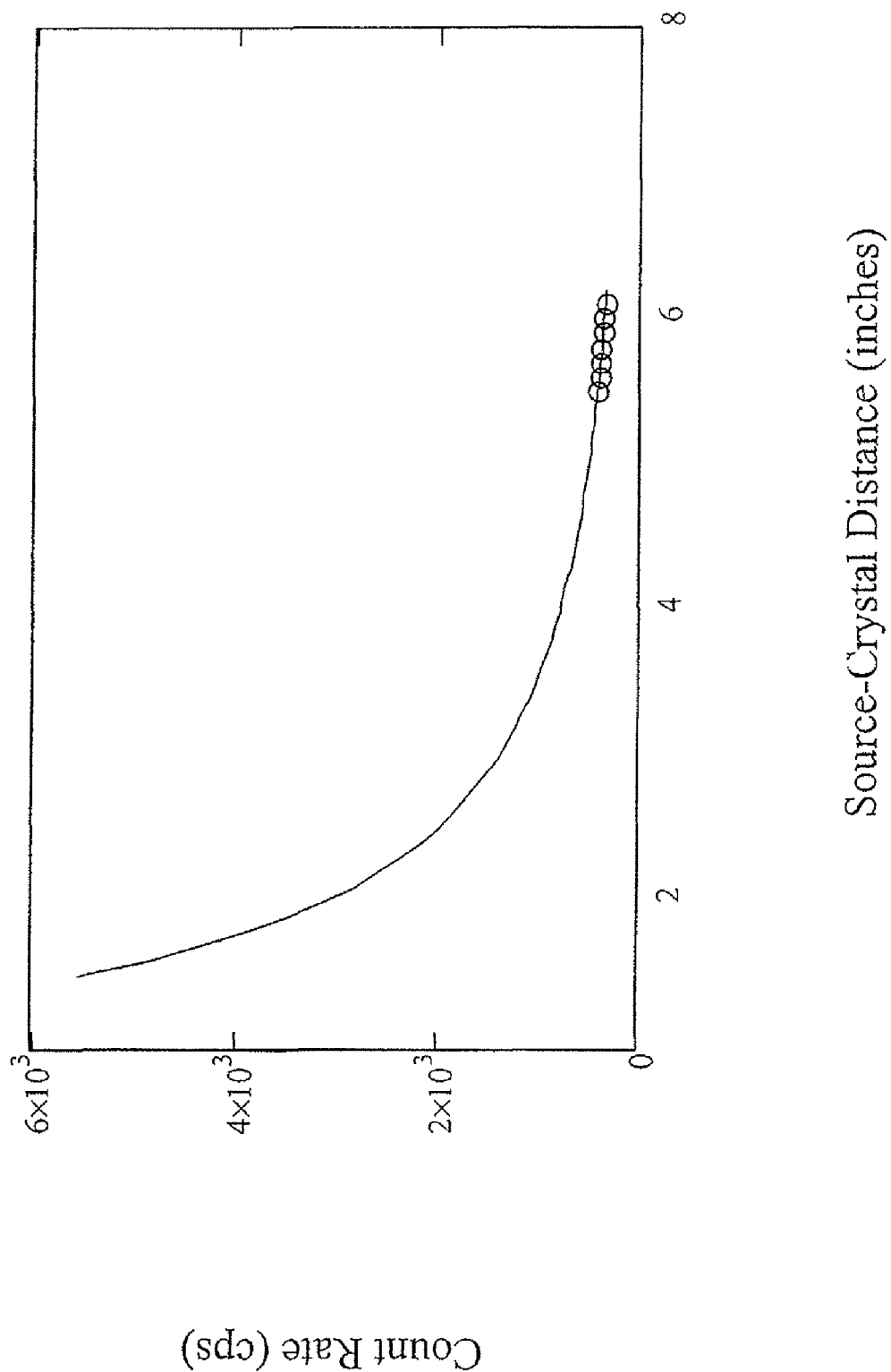
FIG. 3 illustrates the theoretical response curve of FIG. 2, with experimental data.
Figure 4:
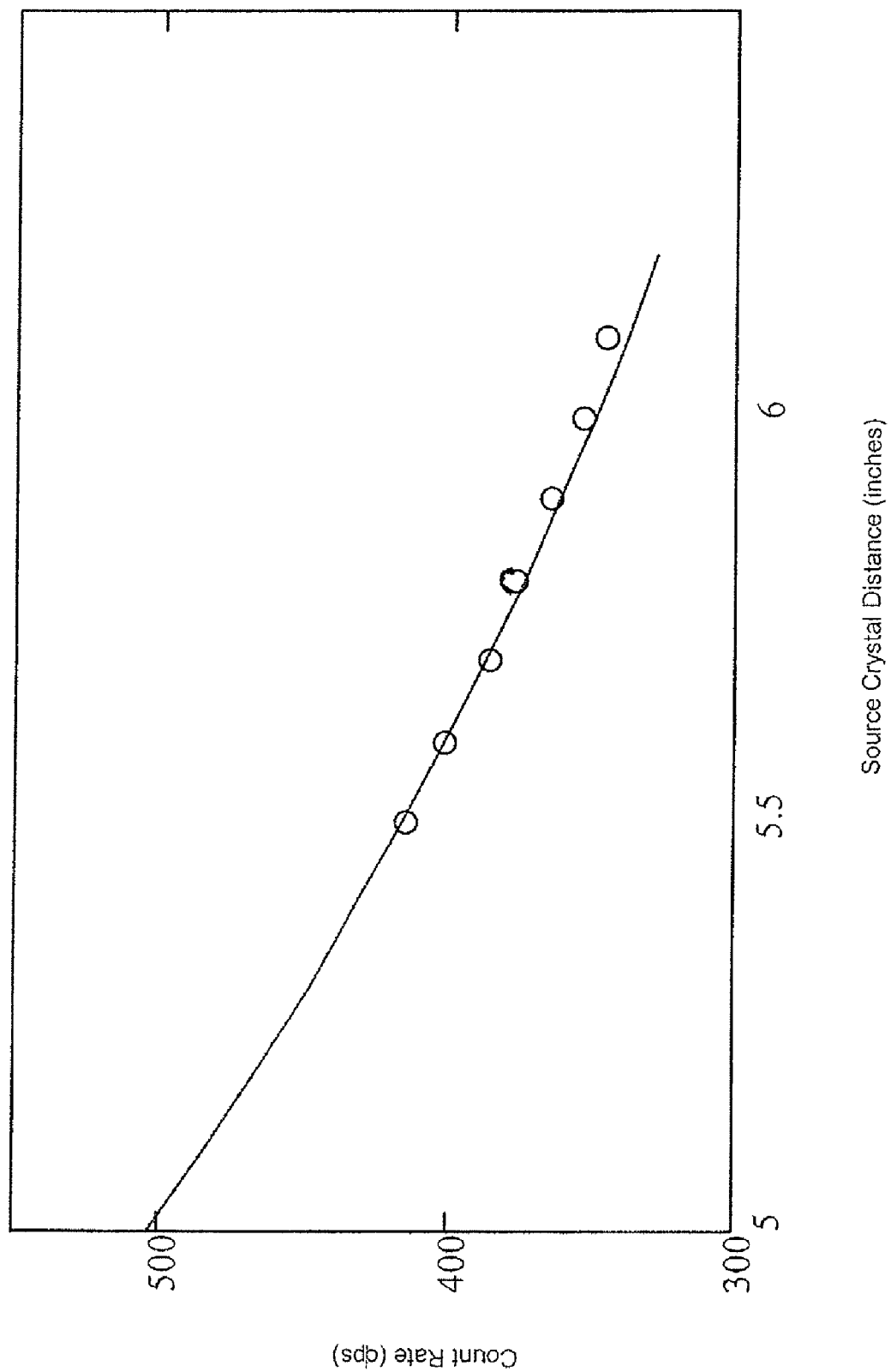
FIG. 4 illustrates the theoretical response curve and data of FIG. 3 on an expanded scale.

FIGS. 2, 3, and 4 illustrate an effect on measured count rates by a detector for a radiation disposed at a variety of distances from the detector along an axis normal to the surface of the sensor. As previously noted, geometric factors affecting the response of a radiation detector to a radiation source include both the radial distance of the source from the surface of the detector, along with the angular position of the source with respect to the axis normal to the sensor surface. FIG. 2 illustrates the theoretical response of a detector count rate (in counts-per-second) versus the distance (in inches) between the source and sensor surface along the normal axis (hereafter, the z-axis) to the sensor. FIG. 3 presents the same theoretical curve (solid line) representing count rate along with its defining equation, as well as data (circles) from experiment. The theoretical curve is generated from the "count rate equation":

$$R = -E/2 * \{[z/\sqrt{(a^2+z^2)}]-1\}$$

where "E" is the product of the total radiation emitted by the test source (in counts per second) which is representative of an aliquot during an injection and the efficiency of the detector, "z" is the distance of the test source along the z-axis (in meters) from the radiation detector, and "a" is the radius of a circle (in meters) having approximately the same surface area as the surface of the radiation detector sensor. This count rate equation describes the amount of gamma radiation incident on a surface of area proportional to $a^2$ at some distance z from a source emitting radiation in all directions. The data in FIG. 3 present data obtained from a $^{57}$Co source held at fixed distance away from a CZT detector crystal. FIG. 4 further expands the abscissa of FIG. 3 and illustrates good agreement between the theoretical curve and the experimental data.

Preferably, an aliquot positioner 302 as shown in FIG. 1a is to be placed in an optimal axial distance with respect to the radiation detector surface. However, as discussed inaccuracies of this positioning may be created. For example, a user may place the positioner in the detector system out of alignment compared to the preferred position. Further, a cassette having a fluid path or other aliquot positioner assembly may be manufactured within some physical tolerance range, so inaccuracies may occur in the actual position of the fluid path with respect to the detector. As illustrated in FIGS. 2-4, the detector response becomes approximately linear over short distance ranges (where mechanical movement or error may occur), as the radiation source is located further and further away from the detector. Thus, small deviations in displacement along the normal axis from the detector will produce less error in the count rate measurements, the further the detector is away. The count rate will decrease, however, as this distance increases for a fixed detector size, and therefore the measurement time will increase (due to Poisson counting statistical requirements). Depending on the application, radioactive pharmaceuticals source, concave fluid path curvature, use of a collimator, and use of an attenuator, an optimal or acceptable distance can be determined.

Figure 5:
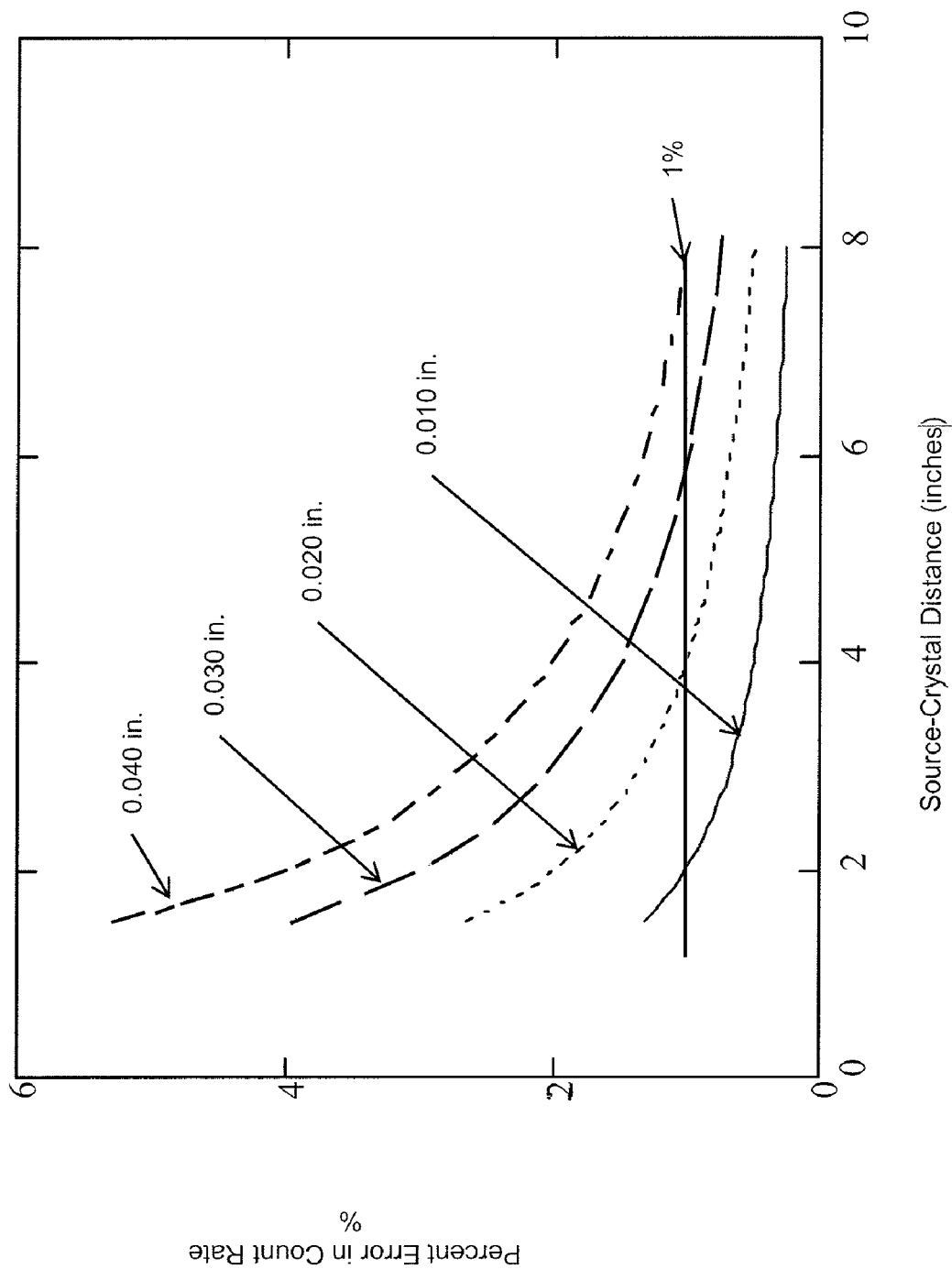
FIG. 5 illustrates the model-based percent error in count rate for various position errors as a function of a distance from the source to a crystal.

FIG. 5 illustrates the effect of small deviations in the distance measurements z-axis) with respect to the detector output. The ordinate provides percent error in the dose (activity) measurement as a function of theoretical distance between the radiation source and the detector along the z-axis. The count rate is represented by three curves and based on the count rate equation and illustrates the percent error from the expected response of the detector at a nominal distance z (in inches) from the source to the curved fluid positioner, if the actual placement of the source is displaced by 0.01, 0.02, 0.03, and 0.04 inches from the preferred position. For these calculations, the radius of an equivalent circular sensor surface is set to 5 mm. For example, in FIG. 5, if the fluid path is approximately six inches from the radiation detector sensor, less than a 2% error from the expected sensor response is obtained for an error of 0.04 inches in the placement of the fluid pathway. These theoretical calculations indicate that the fluid path element is preferably placed in a range of 5 to 8 inches from the detector. In this range, errors in mechanical placement of the fluid path or its fabrication result in a reduced error of detector output.

Figure 6:
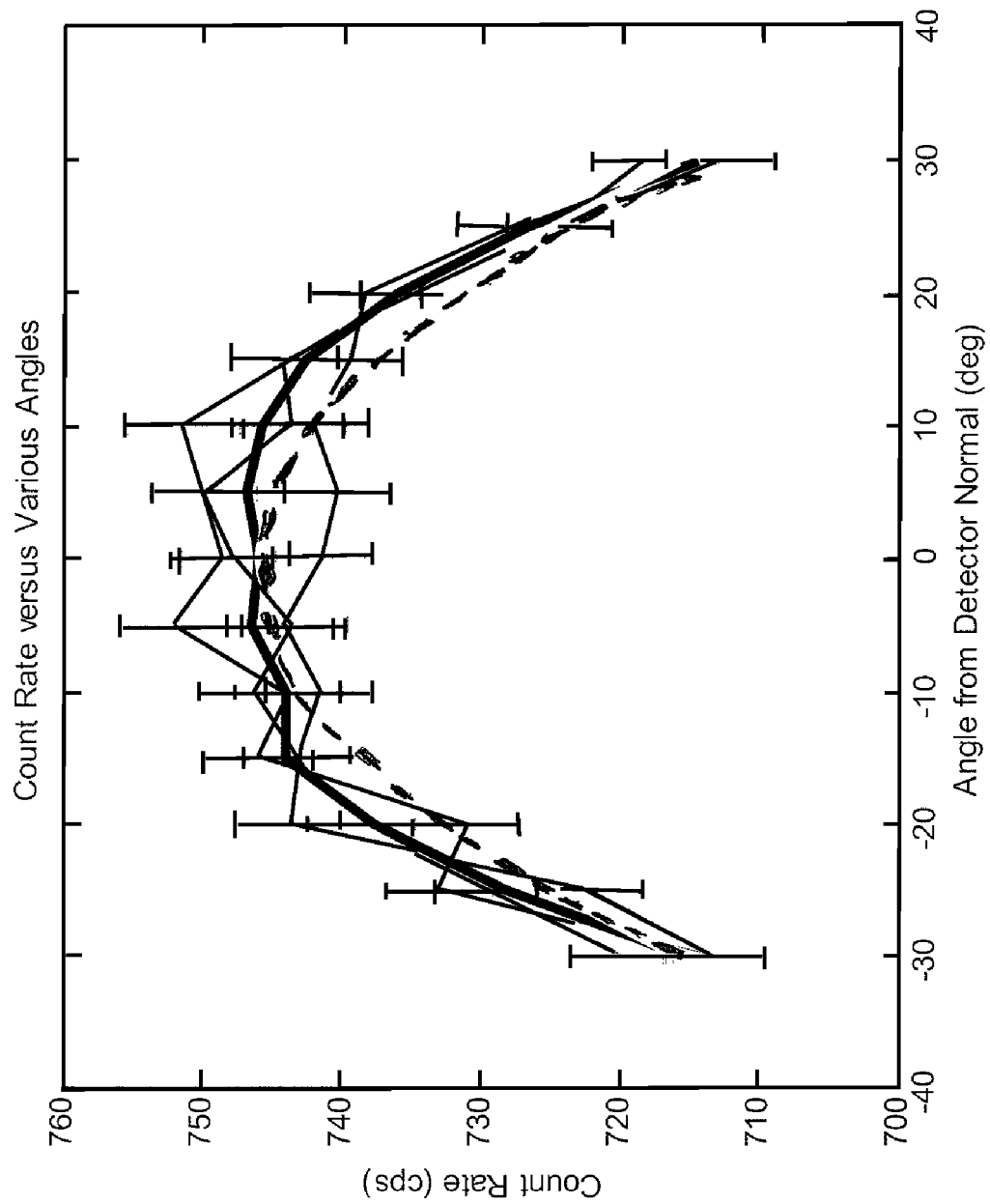
FIG. 6 illustrates experimental data of a response of a CZT detector to a radiation source as a function of an angular displacement about a central axis and a theoretical curve fit to the data based on a root cosine model.
Figure 7:
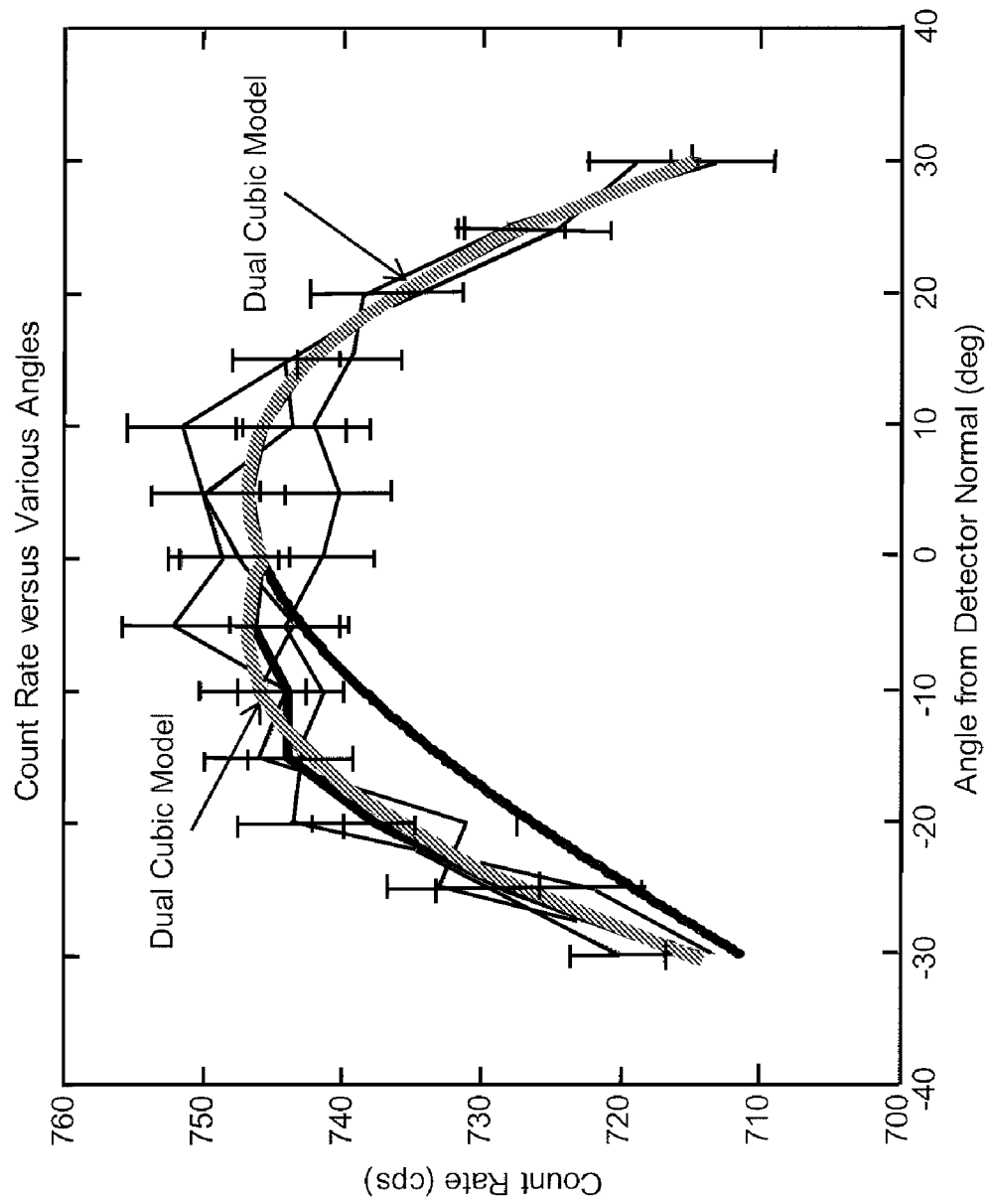
FIG. 7 illustrates the count rate experimental data of FIG. 6 fit to a dual-cubic model.

While FIGS. 2 through 5 are graphs that illustrate effects on the detector response based on a distance of a radiation source or aliquot positioner at a location along a normal axis from the face of a sensor, FIGS. 6 and 7 illustrate the effect on the detector response based on angular displacement of the source about the normal axis (the inclination angle of the source). In FIGS. 6 and 7, the dotted lines with error bars present experimental data from positioning the $^{57}$Co source through a variety of inclination angles with respect to the detector sensor surface. The radial distance of the source to the detector is maintained at six inches. The graphs illustrate the response of the detector (in counts per second) versus the inclination angle (in degrees).

In FIG. 6, a graph illustrates detector response, where the heavy solid line represents the average response versus angle for the accumulated data. The heavy dashed line represents the fit of the data to the count rate model based on a root cosine function. FIG. 7 illustrates the same data and data average, but the model curve is derived from a "Dual Cubic Model." The data in the FIGS. 6 and 7 illustrate a fairly flat detector response (within experimental error) for a source located in the range of ±30° from the center of the detector. The cosine-based model illustrated in FIG. 6 provides one model of this range of response, however, although the dual cubic model illustrated in FIG. 7 appears to fit the data more adequately. The dual cubic model (or any model used to fit the experimental data), which relates count rate to angle for a fixed radius arc, can be used in combination with the count rate equation to solve for a theoretical concave surface profile (which is symmetrical about the z-axis). This theoretical concave profile—based on a dual cubic or other model of the actual angular response of the sensor—optimizes the detector reading of the activity of an aliquot regardless of its position on the concave surface. By using the derived profile using this method, a uniform response, regardless of inclination angle of the source, can be achieved. This will allow the detector system to accurately measure the activity of small or large distributed aliquots that exist in the fluid pathway.

Figure 8:
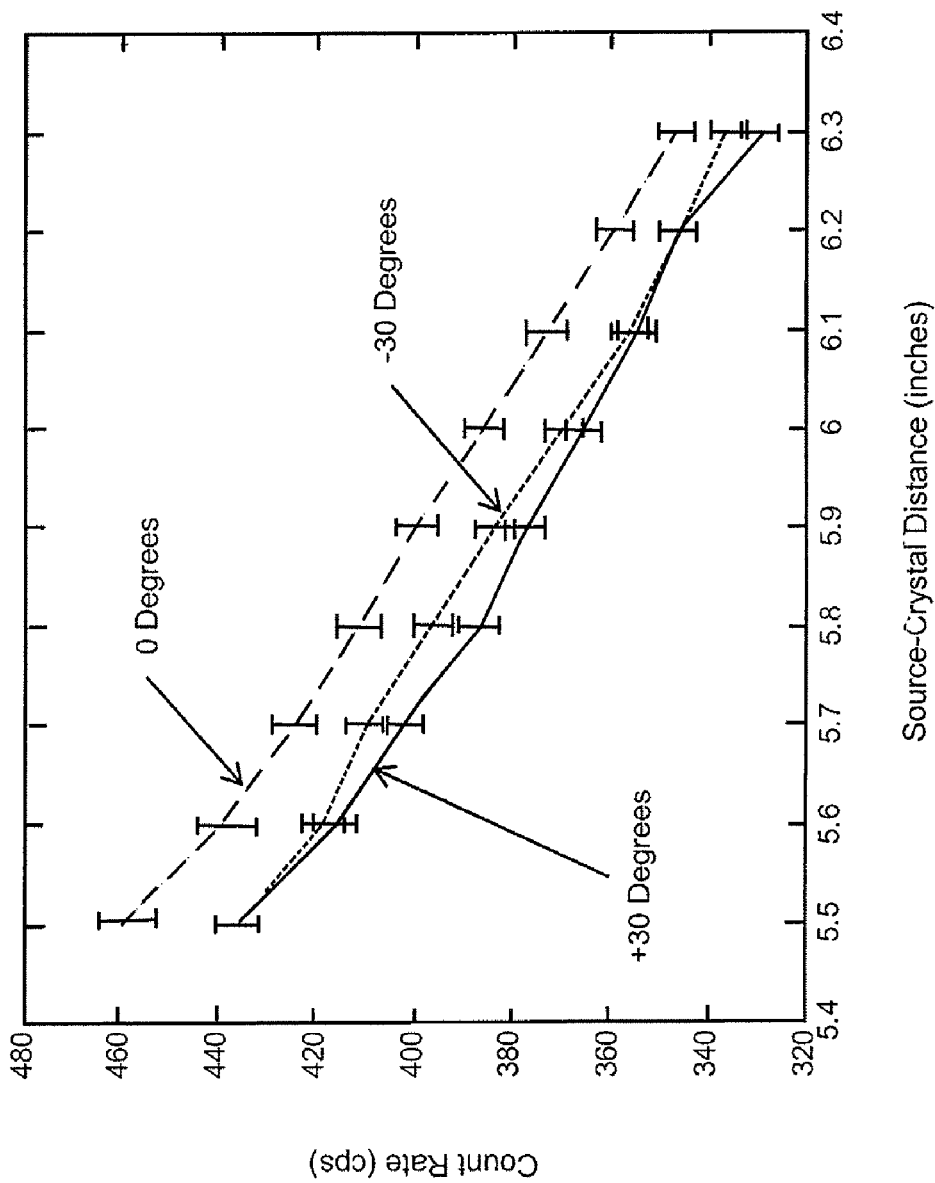
FIG. 8 illustrates count rate experimental data for varying distance at three different source-detector angles (0, +30, −30 degrees).

FIG. 8 graphically combines data for the effect of both linear distance and inclination angle, and illustrates the detector output (in counts-per-second) as a function of linear distance along the z-axis to the sensor face at three different angles. The top curve presents the same experimental data as in FIG. 4. The two bottom curves show the response of the detector if the source is placed at a +30° or −30° inclination angle. The average slope of all three curves in FIG. 8 is similar for various inclination angles. Thus, a change in count rate as a function of a distance from the source to the sensor crystal or radius, is the similar regardless of the inclination angle of the radiation source with respect to the surface of the sensor. The large "radius," therefore, remains useful at a variety of inclination angles.

FIG. 9 is a graph illustrating the use of an attenuator in a detector system. The graph represents the actual response of a detector to a source placed on a curved surface with its centroid positioned a known distance from the detector surface. This models an aliquot of a radiopharmaceutical located within a coiled tube disposed along a dual cubic surface with its centroid six inches from the sensor face. The experimental conditions include interposing a 0.1 inch thick polycarbonate disc between the source (here, $^{57}$Co) and the detector to model the effect of incoherent scatter due to the tubing material. Such a concave fluid path, for example, a coiled tube of polycarbonate plastic, molded along a surface based on a dual-cubic model, and placed six inches or more from the sensor surface—comprises the preferred embodiment of this invention. The graph in FIG. 9 presents the response of the detector in counts per second (the left ordinate) versus the inclination angle of the source in degrees (the abscissa). The ordinate on the right presents the percent deviation of the measured counts from the average of all the data points. The graph illustrates that, regardless of the total error in detector measurement, little or no systematic error due to the angular orientation of the source occurs as long as the source lies upon a suitable curve in space. These data demonstrate a reduction in the measurement error of radioactivity by a detector system that would otherwise be due to geometric factors.

It will be apparent to those skilled in the art that various other embodiments may be contemplated in addition to those described herein without departing from the scope and spirit of this invention. Accordingly, it is not intended that the scope of the claims appended hereto be limited to the description as set forth herein, but rather that the claims be broadly construed.

The invention claimed is:

1. A system for measuring radioactive material, comprising:
   a fluid path for receiving at least one aliquot;
   an aliquot positioner formed with a concave surface and connected to the fluid path and capable of receiving the at least one aliquot therefrom; and
   a detector located at an axial distance from the aliquot positioner and operable to determine the level of radioactivity of the at least one aliquot disposed in the aliquot positioner.

2. The system of claim 1 wherein the detector is proximal to a concave side of the aliquot positioner.

3. The system of claim 1 wherein the aliquot positioner includes a passage formed as a coiled, spiral or serpentine configuration.

4. The system of claim 1 further including an output assembly connected to an output of the aliquot positioner.

5. The system of claim 1 further including a liquid source of radiopharmaceutical in fluid communication with the fluid path.

6. The system of claim 1 further including at least one optical element disposed between the aliquot positioner and the detector.

7. The system of claim 1 wherein the aliquot positioner has a surface based on a parabolic, spherical or dual cubic model.

8. The system of claim 1 wherein the aliquot positioner includes a tubular conduit.

9. The system of claim 1 wherein the aliquot positioner includes a bag.

10. The system of claim 1 further including an injector connected to the fluid path.

11. A system for measuring radioactive material, comprising:
    a fluid path for receiving at least one aliquot releasing radioactive energy;
    a selectable positioner directing the radioactive energy; and
    a detector located at a distance from the selectable positioner and operable to determine the level of radioactivity of the at least one aliquot disposed in the selectable positioner,
    wherein the selectable positioner includes at least one of a variable attenuator or an aliquot positioner having a concave configuration.

12. The system of claim 11 wherein a curvature of the at least variable attenuator and a curvature of the aliquot positioner are varied to optimize radiation detection by the detector.

13. The system of claim 11 wherein the variable attenuator includes channels extending in a radial direction therethrough thereby forming a collimator array.

14. The system of claim 13 wherein the channels are formed of varied diameters.

15. The system of claim 14 wherein the varied diameters are smallest toward a center and larger at a periphery of the variable attenuator.

16. The system of claim 11 wherein the variable attenuator includes a first collimator and a second collimator.

17. A method for measuring activity of an aliquot, comprising:
    forming an aliquot in a concave shaped fluid passage;
    providing a detector a distance from the concave shaped surface; and
    reading spectral energy of the aliquot thereby determining the activity.

18. The method of claim 17 further including inserting an optical element between the concave shaped fluid passage and the detector.

19. The method of claim 17 further including collimating the spectra energy before reading the activity.

* * * * *

UNITED STATES PATENT AND TRADEMARK OFFICE
CERTIFICATE OF CORRECTION

PATENT NO.       : 8,198,599 B2
APPLICATION NO.  : 12/664653
DATED            : June 12, 2012
INVENTOR(S)      : Bouton et al.

It is certified that error appears in the above-identified patent and that said Letters Patent is hereby corrected as shown below:

ON THE FACE PAGE

In Field (57), Line 12, delete "fluid passage.", and insert -- fluid passage is also described." --, therefor.

In Field (57), Line 14, delete "activity is determining", and insert -- activity by determining" --, therefor.

IN THE DRAWINGS

In Fig. 4, Sheet 7 of 13, delete "(c|ps)" and insert -- (cps) --, therefor.

In Fig. 5, Sheet 8 of 13, delete "(inches|)" and insert -- (inches) --, therefor.

In Fig. 6, Sheet 9 of 13, delete "(deg)" and insert -- (deg.) --, therefor.

In Fig. 7, Sheet 10 of 13, delete "(deg)" and insert -- (deg.) --, therefor.

IN THE SPECIFICATION

In Column 13, Line 30, delete "z-axis)" and insert -- z-axis --, therefor.

IN THE CLAIMS

In Claim 1, Column 15, Line 9, delete "determine the level", and insert -- determine a level --, therefor.

In Claim 4, Column 15, Line 17, delete "further including", and insert -- further comprising --, therefor.

Signed and Sealed this
Twelfth Day of February, 2013

Teresa Stanek Rea
*Acting Director of the United States Patent and Trademark Office*

CERTIFICATE OF CORRECTION (continued)
U.S. Pat. No. 8,198,599 B2

IN THE CLAIMS

In Claim 5, Column 15, Line 19, delete "further including", and insert -- further comprising --, therefor.

In Claim 6, Column 15, Line 22, delete "further including", and insert -- further comprising --, therefor.

In Claim 10, Column 15, Line 31, delete "further including", and insert -- further comprising --, therefor.

In Claim 11, Column 16, Line 4, delete "determine the level", and insert -- determine a level --, therefor.

In Claim 18, Column 16, Line 31, delete "further including", and insert -- further comprising --, therefor.

In Claim 19, Column 16, Line 34, delete "further including", and insert -- further comprising --, therefor.